United States Patent
Sagawa et al.

(10) Patent No.: US 9,034,924 B2
(45) Date of Patent: May 19, 2015

(54) N-ACYL BASIC AMINO ACID DISPERSION

(75) Inventors: Koichiro Sagawa, Fort Lee, NJ (US);
Bruce W. Gesslein, Fort Lee, NJ (US);
Kseniya Popova, Fort Lee, NJ (US);
Eiko Oshimura, Kanagawa (JP);
Naoaki Ikeda, Kanagawa (JP);
Tomokazu Kamidoi, Kanagawa (JP)

(73) Assignee: AJINOMOTO CO., LTD., Tokyo (JP)

( * ) Notice: Subject to any disclaimer, the term of this patent is extended or adjusted under 35 U.S.C. 154(b) by 0 days.

(21) Appl. No.: 13/545,309

(22) Filed: Jul. 10, 2012

(65) Prior Publication Data

US 2013/0011355 A1 Jan. 10, 2013

Related U.S. Application Data

(63) Continuation of application No. PCT/US2011/021308, filed on Jan. 14, 2011.

(60) Provisional application No. 61/295,248, filed on Jan. 15, 2010.

(51) Int. Cl.
*A61K 8/44* (2006.01)
*A61Q 5/02* (2006.01)
*A61Q 19/10* (2006.01)

(52) U.S. Cl.
CPC . *A61K 8/442* (2013.01); *A61Q 5/02* (2013.01); *A61Q 19/10* (2013.01)

(58) Field of Classification Search
CPC ........................................................ A61K 8/44
USPC ........................................................ 514/563
See application file for complete search history.

(56) References Cited

U.S. PATENT DOCUMENTS

| 6,555,708 | B1 | 4/2003 | Yamato et al. | |
|---|---|---|---|---|
| 2002/0102295 | A1* | 8/2002 | Niemiec et al. | 424/450 |
| 2003/0206932 | A1 | 11/2003 | Liu et al. | |
| 2005/0265951 | A1 | 12/2005 | Yamawaki et al. | |

FOREIGN PATENT DOCUMENTS

| JP | 61-137812 | 6/1986 |
|---|---|---|
| JP | 61-241396 | 10/1986 |
| JP | 1-242563 | 9/1989 |
| JP | 02-028298 | 1/1990 |
| JP | 8-337519 | 12/1996 |
| WO | 01/14317 | 3/2001 |

OTHER PUBLICATIONS

International Search Report issued in PCT/US2011/021308 on Mar. 29, 2012.
Written Opinion issued in PCT/US2011/021308.

* cited by examiner

*Primary Examiner* — David J Blanchard
*Assistant Examiner* — Tigabu Kassa
(74) *Attorney, Agent, or Firm* — Oblon, McClelland, Maier & Neustadt, L.L.P.

(57) ABSTRACT

Provision of an N-acyl basic amino acid dispersion superior in dispersibility. The present invention provides a production method of an N-acyl basic amino acid dispersion having a pH of 2 to 12, comprising
(1) a step of dissolving an N-acyl basic amino acid in a base solution, and
(2) a step of mixing the obtained N-acyl basic amino acid solution with one or more equivalents of an acid relative to the base.

8 Claims, 4 Drawing Sheets

N-ACYL BASIC AMINO ACID DISPERSION

CROSS REFERENCES TO RELATED APPLICATIONS

This application is a Continuation of International Patent Application No. PCT/US2011/021308, filed on Jan. 14, 2011, and claims priority to U.S. Provisional Patent Application No. 61/295,248, filed on Jan. 15, 2010.

TECHNICAL FIELD

The present invention relates to a production method of an N-acyl basic amino acid dispersion, a dispersion obtained by the production method, and cosmetic or cutting oil containing the dispersion.

BACKGROUND ART

Reduction of friction and resistance in the substrate surface or interface between substrates has currently been an important subject in a number of different technical areas. Lubricants such as oil and grease have been used to reduce friction on hard surfaces such as metal and the like.

Powder lubricants such as boron nitride, nylon powder, molybdenum compound and N-lauroyllysine are also used for the treatment of fibers and hard surfaces. Since these compounds provide lubricity to the skin and hair, they are also used for cosmetics.

Since N-lauroyllysine has a particular plate-like crystal structure, and good slidability resulting therefrom, it is used as a powder material in the fields of cosmetic, lubricant and the like. However, since N-lauroyllysine has high water repellency and is poor in compatibility with water, it cannot be blended with an aqueous composition with ease and addition thereof at a high concentration is not available. Moreover, since N-lauroyllysin agglomerates in the obtained aqueous composition, the composition problematically lacks smooth texture.

Patent document 1 describes an embodiment wherein N-mono long-chain acyl basic amino acid crystals are appropriately pulverized, and used as a pearlizer in shampoo. However, it is still difficult to contain N-mono long-chain acyl basic amino acid stably at a concentration of not less than 5%, and the aforementioned problems remain unsolved.

On the other hand, patent document 2 proposes a method of neutralization crystallization of N-mono long-chain acyl basic amino acid to give ultrafine crystals to be added to cosmetics. As a method for obtaining crystals by neutralization-crystallization, patent document 3 describes a method including adding crude crystals of N-lauroyllysine to an aqueous medium at pH 11 or above, heating the mixture with stirring to 40 to 60° C. to dissolve the crystals, and neutralizing the mixture to pH 6.5 by dropwise addition of hydrochloric acid to allow crystallization. Patent document 4 describes a method of controlling the crystal diameter of $N^\epsilon$-long chain acyllysine by changing the crystallization conditions.

However, all these techniques aim to obtain crystal with a particular size and a particular shape in the form of a powder, rather than solve the problems of N-lauroyllysine such as poor compatibility with water and agglomeration and settling in a dispersion of N-lauroyllysine. Therefore, it is still difficult to contain N-lauroyllysine at a high concentration in cosmetics, and the problem of agglomeration in the composition remains unsolved.

DOCUMENT LIST

Patent Document patent document 1: JP-A-61-137812
patent document 2: JP-A-8-337519
patent document 3: JP-A-1-242563
patent document 4: WO2001/14317

SUMMARY OF THE INVENTION

Problems to be Solved by the Invention

The problem to be solved by the present invention is to provide an N-acyl basic amino acid dispersion superior in the dispersibility. Moreover, the problem is to provide a cosmetic or cutting oil superior in dispersibility, in which N-acyl basic amino acid does not coagulate or settle, by utilizing the dispersion.

Means of Solving the Problems

The present inventors have conducted intensive studies in an attempt to solve the aforementioned problems and found that a dispersion obtained by dissolving an N-acyl basic amino acid in a base solution, and then mixing the obtained N-acyl basic amino acid solution with a particular amount of an acid shows remarkably superior dispersibility, which resulted in the completion of the present invention.

Accordingly, the present invention includes the following embodiments.

[1] A method of producing an N-acyl basic amino acid dispersion having a pH of 2 to 12, which comprises
  (1) a step of dissolving an N-acyl basic amino acid in a base solution, and
  (2) a step of mixing the obtained N-acyl basic amino acid solution with one or more equivalents of an acid relative to the base.
[2] The method of the above-mentioned [1], wherein the concentration of the N-acyl basic amino acid in the dispersion is 3 to 30 wt %.
[3] The method of the above-mentioned [1], wherein (viscosity at 3 rpm)/(viscosity at 30 rpm) of the dispersion is within the range of 4 to 30.
[4] The method of the above-mentioned [1], wherein the base is sodium hydroxide or potassium hydroxide, and the amount of the base in the base solution is 0.05 g to 1 g per 1 g of the N-acyl basic amino acid.
[5] The method of the above-mentioned [1], wherein the acid is an organic acid.
[6] The method of the above-mentioned [1], wherein the acid is at least one selected from lactic acid, citric acid, ascorbic acid, 2-pyrrolidone-5-carboxylic acid, an acidic amino acid and a mono salt thereof, an N-acyl amino acid and an N-acyl acidic amino acid mono salt.
[7] The method of the above-mentioned [1], wherein the acid is an N—$C_{8-22}$ acyl glutamic acid mono salt.
[8] The method of the above-mentioned [1], wherein the N-acyl basic amino acid solution comprises a surfactant.
[9] The method of the above-mentioned [8], wherein the surfactant is an alkylglucoside.
[10] The method of the above-mentioned [1], wherein the N-acyl basic amino acid is $N^\epsilon$-lauroyllysine.
[11] The method of the above-mentioned [1], wherein the acid is added dropwise to the N-acyl basic amino acid solution at the rate of not less than 0.1 mmol/sec per 1 dl of the N-acyl basic amino acid solution.

[12] An N-acyl basic amino acid dispersion comprising 10 to 30 wt % of an N-acyl basic amino acid, which has a pH of 2 to 12, and (viscosity at 3 rpm)/(viscosity at 30 rpm) of 4 to 30.

[13] An N-acyl basic amino acid dispersion obtained by the method of any of the above-mentioned [1] to [11].

[14] A cosmetic comprising the N-acyl basic amino acid dispersion of the above-mentioned [12] or [13].

[15] A cutting oil comprising the N-acyl basic amino acid dispersion of the above-mentioned [12] or [13].

[21] A method of producing an N-acyl basic amino acid dispersion, which comprises
(1) a step of dissolving an N-acyl basic amino acid in an alkaline solution having a pH of 9 or more, and
(2) a step of adjusting the pH of the solution to 4 to 8 with an organic acid.

[22] The method of the above-mentioned [21], wherein the organic acid used to adjust the pH is selected from lactic acid, citric acid, ascorbic acid, 2-pyrrolidone-5-carboxylic acid, an acidic amino acid, an N-acyl amino acid, an N-acyl acidic amino acid mono salt and a mixture thereof.

[23] The method of the above-mentioned [21], wherein the organic acid used to adjust the pH is an N—$C_{8-22}$ acyl glutamic acid mono salt.

[24] The method of any of the above-mentioned [21] to [23], wherein the N-acyl basic amino acid solution comprises a surfactant.

[25] The method of the above-mentioned [24], wherein the surfactant is an alkylglucoside.

[26] The method of any of the above-mentioned [21] to [25], wherein the N-acyl basic amino acid is $N^\epsilon$-lauroyllysine.

[27] The method of any of the above-mentioned [21] to [26], wherein the pH is adjusted by adding dropwise the N-acyl basic amino acid solution to an organic acid, or adding dropwise an organic acid to the N-acyl basic amino acid solution, over 10 min to 4 hr.

[28] An N-acyl basic amino acid dispersion obtained by the method of any of the above-mentioned [21] to [27].

[29] A cosmetic comprising the N-acyl basic amino acid dispersion of the above-mentioned [28].

[30] A cutting oil comprising the N-acyl basic amino acid dispersion of the above-mentioned [28].

Effect of the Invention

According to the present invention, an N-acyl basic amino acid dispersion superior in dispersibility can be obtained, and a dispersion containing an N-acyl basic amino acid at a high concentration can be obtained. Utilizing the dispersion, moreover, an N-acyl basic amino acid can be blended with a cosmetic such as shampoo and the like or a cutting oil without causing problems of agglomeration and settling, whereby a cosmetic or cutting oil superior in dispersibility and improved in smooth texture can be obtained.

In addition, using an organic acid as the acid, an N-acyl basic amino acid dispersion can be obtained easily, and a dispersion more superior in lubricity can be obtained. By utilizing the dispersion, a cosmetic or cutting oil superior in smooth texture can be obtained.

DESCRIPTION OF EMBODIMENTS

Figure 1:
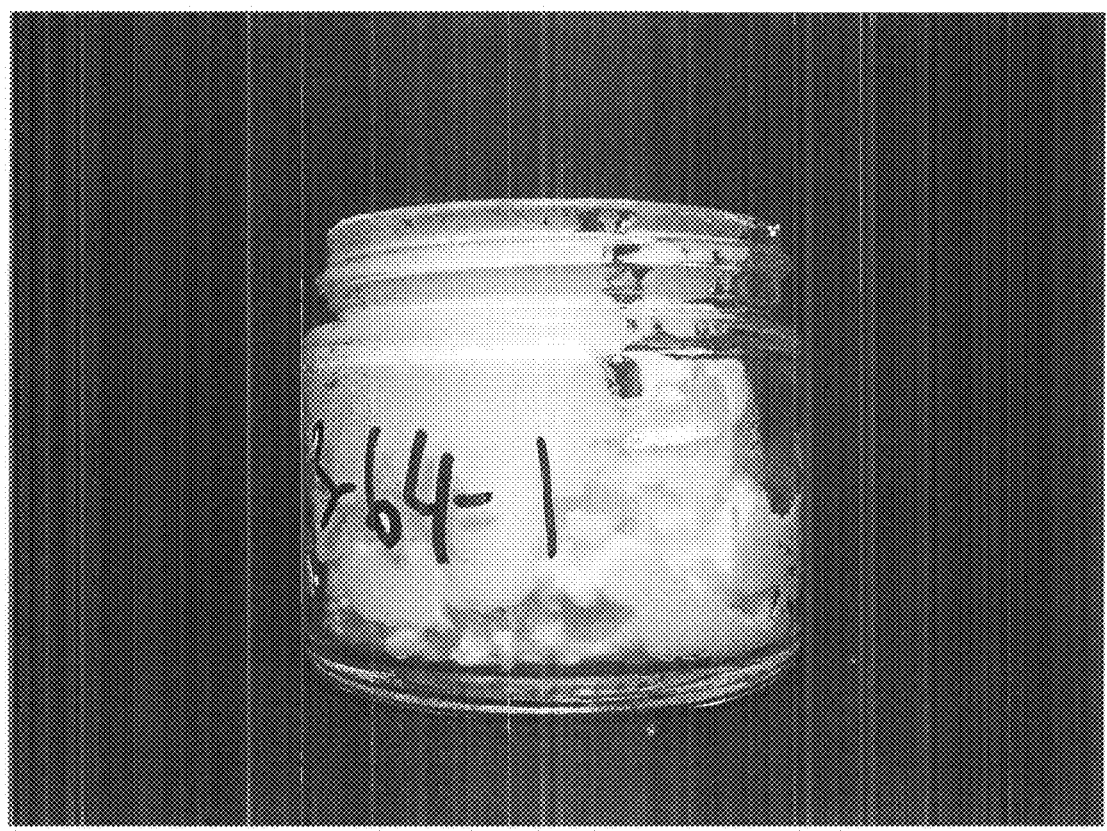
FIG. 1 is a photograph of the dispersion of Example 1 after a lapse of one month.

The present invention provides a production method of an N-acyl basic amino acid dispersion comprising a step of dissolving an N-acyl basic amino acid in a base solution (dissolution step), and a step of mixing the obtained N-acyl basic amino acid solution with a particular amount of an acid (mixing step), as well as an N-acyl basic amino acid dispersion obtained by the production method, and further provides a cosmetic or cutting oil containing the dispersion.

In the present specification, the dispersion refers to one wherein the N-acyl basic amino acid is uniformly present in a fine particle state in a solvent. The solvent is preferably an aqueous solvent, and examples thereof include water, hydrophilic organic solvents and mixtures thereof. Examples of the hydrophilic organic solvent include lower alcohols such as methanol, ethanol, propanol, butanol, isopropanol and the like; polyvalent alcohols such as ethylene glycol, glycerol, 1,3-butyleneglycol and the like; lower ketones such as acetone, ethyl methyl ketone and the like; and mixtures thereof. The solvent is preferably water alone.

(Dissolution Step)

For the production of the N-acyl basic amino acid dispersion of the present invention, an N-acyl basic amino acid is first dissolved in a base solution.

Examples of the basic amino acid of the N-acyl basic amino acid include lysine, ornithine, arginine, histidine and the like. These can be used irrespective of L-form, D-form or racemate. From the aspects of lubricity, lysine and arginine are preferable, lysine is more preferable, and L-lysine and D-lysine are particularly preferable.

The acyl group of the N-acyl basic amino acid is preferably a $C_{8-22}$ acyl group, which may be a straight chain or a branched chain, or an acyl group derived from a saturated fatty acid or an acyl group derived from an unsaturated fatty acid. Examples of the $C_{8-22}$ acyl group include decanoyl, lauroyl, myristoyl, palmitoyl, stearoyl, oleoyl, behenoyl, coconut fatty acid acyl, palm kernel oil fatty acid acyl, beef tallow fatty acid acyl and the like. Since the starting material can be widely available, lauroyl is preferable. An N-acyl basic amino acid can be synthesized by using a basic amino acid and a $C_{8-22}$ fatty acid, as described in JP-A-49-1513. Examples of the utilizable $C_{8-22}$ fatty acid include straight chain fatty acids such as decanoic acid, lauric acid, myristic acid, palmitic acid, stearic acid, oleic acid, behenic acid, coconut fatty acid, palm kernel oil fatty acid, beef tallow fatty acid and the like, and mixtures thereof. From the aspects of lubricity and conditioning ability, decanoic acid, lauric acid, myristic acid and palmitic acid are preferable, and lauric acid is particularly preferable.

The acyl group may be bonded to any of the α-amino group and the amino group in the side chain of the basic amino acid.

Examples of the commercially available N-acyl basic amino acid include $N^\epsilon$-lauroyllysine (manufactured by Ajinomoto Co., Inc., trade name "Amihope LL"), $N^\alpha$-lauroylarginine (manufactured by Ajinomoto Co., Inc., trade name "Amisafe AL-01") and the like.

The base in the base solution is not particularly limited as long as it can dissolve an N-acyl basic amino acid. Preferred are alkali metal hydroxides such as sodium hydroxide, potassium hydroxide and the like; and alkaline earth metal hydroxides such as calcium hydroxide, magnesium hydroxide and the like. Among these, alkali metal hydroxides such as sodium hydroxide, potassium hydroxide and the like are preferable. An organic base such as trimethylamine, triethylamine, ethanolamine, diethanolamine, triethanolamine, cyclohexylamine, dicyclohexylamine and the like; and a basic amino acid such as arginine, lysine, ornithine, histidine and the like can be used in combination.

Preferably, the base to be used is sodium hydroxide or potassium hydroxide, and the amount thereof in the base solution is 0.05 g to 1 g per 1 g of the N-acyl basic amino acid. When it is less than 0.05 g, the N-acyl basic amino acid may not be dissolved, and when it exceeds 1 g, an acid for neutralization is used more than necessary. Preferably, it is 0.15 g to 0.5 g per 1 g of the N-acyl basic amino acid.

Examples of the solvent for the base solution include water, hydrophilic organic solvents and mixtures thereof. Examples of the hydrophilic organic solvent include lower alcohols such as methanol, ethanol, propanol, butanol, isopropanol and the like; polyvalent alcohols such as ethylene glycol, glycerol, 1,3-butyleneglycol and the like; lower ketones such as acetone, ethyl methyl ketone and the like, and mixtures thereof. When a mixed solvent of water and a hydrophilic organic solvent is used, the mixing ratio is not particularly limited. For example, water:hydrophilic organic solvent is within the range of 70:30 to 30:70. The solvent is preferably water alone.

The concentration of the N-acyl basic amino acid in the N-acyl basic amino acid solution obtained in the dissolution step is preferably within the range of not more than 35 wt %. The concentration is appropriately controlled such that the obtained dispersion has an N-acyl basic amino acid concentration of 3 to 30 wt %, preferably 10 to 30 wt %, more preferably 12 to 25 wt %.

The temperature for the dissolution step of the N-acyl basic amino acid is not particularly limited as long as it can dissolve, and it is preferably within the range of 15° C. to 80° C. For dissolution at high concentration, it is preferably within the range of 20° C. to 80° C., particularly preferably within the range of 25° C. to 80° C. To avoid decomposition and coloring of the N-acyl basic amino acid, dissolution without heating is preferable.

(Mixing Step)

Then, the obtained N-acyl basic amino acid solution is mixed with an acid.

In the mixing step, the N-acyl basic amino acid solution is mixed with one or more equivalents of an acid relative to the base. When the amount is less than one equivalent, hexagonal plate-like crystal is formed, and crystal agglomeration and precipitation easily occur. The upper limit of the acid is preferably 6 equivalents. When it exceeds 6 equivalents, needle crystals may be formed, and lubricity cannot be expected. Moreover, since the crystal form changes in the dispersion, crystal agglomeration or precipitation easily occurs. The amount is preferably 1.05 to 5 equivalents, more preferably 1.25 to 4.5 equivalents, relative to the base, since it improves compatibility with water of the dispersion and dispersibility thereof.

Examples of the acid include inorganic acids such as hydrochloric acid, sulfuric acid and the like and organic acids. An organic acid is preferably used, since the pH of the obtained dispersion can be controlled easily and the obtained dispersion shows superior agglomeration ability and superior lubricity. The organic acid only needs to have a functional group that functions as an acid in a molecule, and examples thereof include acetic acid, lactic acid, citric acid, succinic acid, ascorbic acid; acidic amino acids such as glutamic acid, aspartic acid, 2-pyrrolidone-5-carboxylic acid and the like, and mono salts thereof; N-acyl amino acids; N-acyl acidic amino acid mono salts; polymer acids such as polyacrylic acid, alginic acid and the like; alkyl phosphates and the like. Examples of the N-acyl amino acid include N-acylglutamic acid, N-acylaspartic acid and the like. Here, the acyl group is preferably a $C_{8-22}$ acyl group (e.g., decanoyl, oleoyl, lauroyl, myristoyl, palmitoyl, stearoyl, behenoyl, coconut fatty acid acyl, palm kernel oil fatty acid acyl, beef tallow fatty acid acyl etc.). Examples of the N-acyl acidic amino acid mono salt include N-acylglutamic acid mono salts, N-acylaspartic acid mono salts and the like. Here, the acyl group is preferably a $C_{8-22}$ acyl group (e.g., decanoyl, oleoyl, lauroyl, myristoyl, palmitoyl, stearoyl, behenoyl, coconut fatty acid acyl, palm kernel oil fatty acid acyl, beef tallow fatty acid acyl etc.). The organic acid is preferably lactic acid, citric acid, ascorbic acid, 2-pyrrolidone-5-carboxylic acid, an acidic amino acid or a mono salt thereof, an N-acyl amino acid or an N-acyl acidic amino acid mono salt, more preferably citric acid, an acidic amino acid mono salt (preferably, a glutamic acid mono salt, particularly sodium glutamate) or an N-acyl acidic amino acid mono salt, further more preferably an N—$C_{8-22}$ acylglutamic acid mono salt (e.g., an N-lauroylglutamic acid mono salt, an N-myristoylglutamic acid mono salt, an N-palmitoylglutamic acid mono salt, an N-cocoylglutamic acid mono salt), particularly preferably an N-cocoylglutamic acid mono salt. Examples of the salt include alkali metal salts such as sodium salt, potassium salt and the like; ammonium salt; organic base addition salts such as trimethylamine salt, triethylamine salt, ethanolamine salt, diethanolamine salt, triethanolamine salt, cyclohexylamine salt, dicyclohexylamine salt and the like; and the like, with preference given to sodium salt, potassium salt and triethanolamine salt. Specific preferable examples of the N-cocoylglutamic acid mono salt include N-cocoylglutamic acid monotriethanolamine salt, monosodium N-cocoylglutamate and monopotassium N-cocoylglutamate.

In the mixing step, the N-acyl basic amino acid solution may be added to an acid (preferably an organic acid), or an acid (preferably an organic acid) may be added to the N-acyl basic amino acid solution.

The temperature for the addition is preferably within the range of 10° C. to 80° C., more preferably within the range of 20° C. to 60° C. To avoid decomposition and coloring of the N-acyl basic amino acid, mixing without heating is preferable. The temperature is specifically within the range of 20° C. to 30° C., particularly preferably 25° C.

The time necessary for the mixing step can be appropriately set according to the practical scale, such that crystal does not grow, precipitation does not occur, and rapid agglomeration does not occur. For example, when an acid is added to the N-acyl basic amino acid solution, the acid is preferably added dropwise at the rate of not less than 0.1 mmol/sec per 1 dl of the N-acyl basic amino acid solution. For example, an acid is added dropwise at the rate of 0.1 mmol/sec to 1 mmol/sec per 1 dl of the N-acyl basic amino acid solution. Preferably, the rate is 0.1 mmol/sec to 0.6 mmol/sec per 1 dl of the N-acyl basic amino acid solution. When the rate of dropwise addition is too slow, N-acyl basic amino acid crystal grows and precipitates, thus possibly failing to improve compatibility with water. In particular, an acid is preferably added dropwise as fast as possible until the pH of the N-acyl basic amino acid solution reaches 13 or lower.

After mixing with an acid, a solvent can be appropriately added to control the concentration of the N-acyl basic amino acid in the dispersion.

The mixing step is preferably performed in the presence of a surfactant. In this way, the stability of the finally-obtained N-acyl basic amino acid dispersion can be further improved, thus enabling a long-term storage. In consideration of the storage stability and thermostability over a long period, the proportion of N-acyl basic amino acid to the total amount of surfactants is preferably 15 wt % or more, more preferably 25 wt % or more, particularly preferably 30 wt % or more. Also, it is preferably 1500 wt % or lower, more preferably 1300 wt % or lower.

The surfactant only needs to be contained in the N-acyl basic amino acid solution, and may be added to the N-acyl basic amino acid solution or added during the dissolution step of N-acyl basic amino acid.

The surfactant is not particularly limited as long as the obtained N-acyl basic amino acid dispersion is stable during the mixing step. Examples thereof include anionic surfactants, cationic surfactants, amphoteric surfactants and nonionic surfactants.

Examples of the anionic surfactant include N-long-chain acyl amino acid salts such as N-long-chain acyl acidic amino acid salts (e.g., N-long-chain acylglutamate, N-long-chain acylaspartate), N-long-chain acyl neutral amino acid salts (e.g., N-long-chain acylglycine salts, N-long-chain acylalanine salts, N-long-chain acylthreonine salts), N-long-chain fatty acid acyl-N-methyltaurine salts and the like; alkyl sulfates and alkylene oxide adducts thereof (e.g., sodium laureth sulfate etc.); fatty acid amide ether sulfates; metal salts or weakly basic salts of fatty acid; sulfosuccinic acid surfactants; alkyl phosphates and alkylene oxide adducts thereof; alkylethercarboxylic acids and the like. Here, the acyl group is preferably a $C_{8-22}$ acyl group (e.g., decanoyl, oleoyl, lauroyl, myristoyl, palmitoyl, stearoyl, behenoyl, coconut fatty acid acyl, palm kernel oil fatty acid acyl, beef tallow fatty acid acyl etc.). The alkyl group is preferably a $C_{8-22}$ alkyl group (e.g., decyl group, oleyl group, lauryl group, myristyl group, palmityl group, stearyl group, behenyl group etc.). The anionic surfactant is preferably an N-long-chain acyl amino acid salt, an alkyl sulfate or an alkylene oxide adduct thereof, or an alkyl phosphate or an alkylene oxide adduct thereof.

Examples of the cationic surfactant include aliphatic amine salts (e.g., alkylammonium chloride, dialkylammonium chloride etc.) and quaternary ammonium salts thereof (e.g., cetyltrimethylammonium chloride etc.); aromatic quaternary ammonium salts (e.g., benzalkonium salt etc.); fatty acid acyl arginine esters; alkyloxyhydroxypropylarginine salts and the like. The cationic surfactant is preferably an aliphatic amine salt, especially preferably an aliphatic quaternary ammonium salt.

Examples of the amphoteric surfactant include betaine surfactants such as alkylbetaines, alkylamide betaines, aminopropionate, carboxybetaine and the like, (e.g., cocamidopropylbetaine, cocobetaine etc.); aminocarboxylic acid surfactants (e.g., sodium cocoamphoacetate etc.); and imidazoline surfactants. The amphoteric surfactant is preferably a betaine surfactant.

Examples of the nonionic surfactant include ether surfactants such as glycerol ethers and alkylene oxide adducts thereof and the like; ester surfactants such as glycerol esters and alkylene oxide adducts thereof and the like; ether ester surfactants such as sorbitan esters and alkylene oxide adducts thereof and the like; ester surfactants such as polyoxyalkylene fatty acid esters, glycerol esters, fatty acid polyglycerol esters, acyl amino acid polyglycerol esters, sorbitan esters, fatty acid sucrose esters and the like; alkylglucosides; hydrogenated castor oil pyroglutamic acid diesters and ethylene oxide adducts thereof; nitrogen-containing nonionic surfactants such as fatty acid alkanolamides and the like, and the like. Here, the acyl group is preferably a $C_{8-22}$ acyl group (e.g., decanoyl, oleoyl, lauroyl, myristoyl, palmitoyl, stearoyl, behenoyl, coconut fatty acid acyl, palm kernel oil fatty acid acyl, beef tallow fatty acid acyl etc.). The alkyl group is preferably a $C_{8-22}$ alkyl group (e.g., decyl group, oleyl group, lauryl group, myristyl group, palmityl group, stearyl group, behenyl group etc.). The fatty acid is preferably a $C_{8-22}$ fatty acid (e.g., decanoic acid, lauric acid, myristic acid, palmitic acid, stearic acid, oleic acid, behenic acid, coconut fatty acid, palm kernel oil fatty acid, beef tallow fatty acid etc.). The nonionic surfactant is preferably an alkylglucoside or a fatty acid alkanolamide. The alkylglucoside is preferably a $C_{8-22}$ alkylglucoside, particularly decylglucoside or laurylglucoside. The fatty acid alkanolamide is preferably a $C_{8-22}$ fatty acid alkanolamide, particularly preferably coconut fatty acid diethanolamide.

These surfactants may be used alone or in a mixture of two or more thereof.

Among the surfactants, betaine amphoteric surfactants and nonionic surfactants are preferably used. To achieve a stable dispersibility, a $C_{8-22}$ alkylglucoside is more preferable, and decylglucoside and laurylglucoside are particularly preferable.

(Dispersion Obtained by the Production Method of the Present Invention)

The dispersion obtained by the production method of the present invention has a pH of 2 to 12. When the pH is less than 2, needle crystals may be formed, and lubricity cannot be expected. Moreover, since the crystal form changes in the dispersion, crystal agglomeration or precipitation easily occurs. When the pH exceeds 12, compatibility with water is not improved. The pH is preferably within the range of 3 to 10, more preferably within the range of 4 to 8.

The dispersion obtained by the production method of the present invention preferably contains 3 to 30 wt % of N-acyl basic amino acid. When the content exceeds 30 wt %, agglomeration or precipitation of crystal easily occurs. When it is 10 wt % or more, the dispersion shows a creamy appearance, and is remarkably superior in dispersibility. Thus, the content is preferably 10 to 30 wt %, more preferably 12 to 25 wt %.

The dispersion obtained by the production method of the present invention preferably shows a ratio of viscosities measured at 3 rpm and 30 rpm ((viscosity at 3 rpm)/(viscosity at 30 rpm)) of 4 to 30 using a B-type viscometer No. 4 spindle at 25° C. When the viscosity ratio is within this range, the dispersion shows a creamy appearance, and is remarkably superior in dispersibility. When the viscosity ratio is less than 4, the N-acyl basic amino acid and the solvent are easily separated, and when the viscosity ratio exceeds 30, the dispersion cannot be uniformly blended with a composition such as cosmetic and the like with ease. The viscosity ratio is more preferably within the range of 4 to 10, still more preferably within the range of 5 to 8.

(Cutting Oil and Cosmetic Using the Dispersion Obtained by the Production Method of the Present Invention)

A further step such as purification and the like can be applied to the N-acyl basic amino acid dispersion obtained by the present invention. The obtained dispersion can be used by directly adding to cosmetic or cutting oil.

For addition to a cosmetic, the dispersion is added such that the proportion of the N-acyl basic amino acid to the total amount of the cosmetic composition is 0.01 to 10 wt %. When it is less than 0.01 wt %, the effect derived from N-acyl basic amino acid cannot be afforded, and when it exceeds 10 wt %, the cosmetic may not be improved in the smooth texture and absorbency, and may fail to reduce greasiness. For addition to a cutting oil, the dispersion is added such that the proportion of N-acyl basic amino acid to the total amount of the cutting oil is 0.01 to 10 wt %. In view of lubricity, the dispersion is added such that the proportion is more preferably 1.0 to 5.0 wt %.

When the dispersion obtained by the production method of the present invention is used by directly adding to cosmetic or cutting oil, other components can be added as long as the effect of the present invention is not impaired. Examples of other components include oil, surfactant, powder, pigment, dye, alcohol, preservative, flavor and the like.

EXAMPLES

The present invention is explained in detail in the following by referring to Examples, which are not to be construed as limitative. Unless otherwise specified, the blending amounts in Tables are in unit g. Unless otherwise specified in the present specification, moreover, % means wt %.

Figure 2:
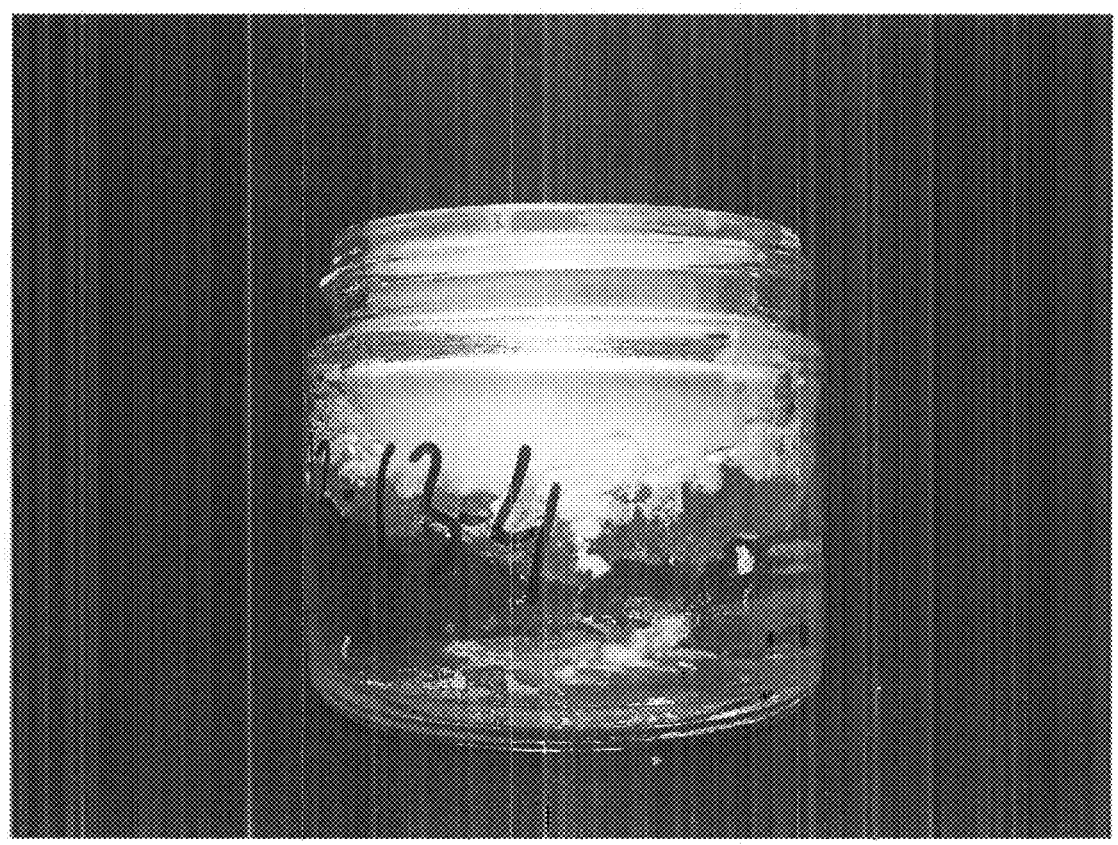
FIG. 2 is a photograph of the dispersion of Comparative Example 1 immediately after production.

Sodium hydroxide (6 g) was dissolved in distilled water (64 g), $N^\epsilon$-lauroyllysine (30 g) was added, and the mixture was stirred at room temperature to complete dissolution to give a uniform transparent solution. To the uniform transparent solution (82.8 g) was slowly added dropwise a 60% aqueous citric acid solution (17.2 g) with stirring over 30 min to give a dispersion (pH 4) containing $N^\epsilon$-lauroyllysine (24.8%) uniformly dispersed therein (Example 1). As a comparison control 60% aqueous citric acid solution, sodium hydroxide and $N^\epsilon$-lauroyllysine powder were mixed at once to give a dispersion having the same mixing ratio as in Example 1 (Comparative Example 1). Example 1 and Comparative Example 1 were preserved at 25° C. for 1 month, and the appearance was observed. A photograph of the dispersion of Example 1 after a lapse of one month is shown in FIG. 1, and a photograph of the dispersion of Comparative Example 1 immediately after preparation is shown in FIG. 2.

The dispersion of Example 1 showed a creamy appearance, and was free of separation even after lapse of one month. However, the dispersion of Comparative Example 1 could not disperse $N^\epsilon$-lauroyllysine. It has been clarified that a simple mixing cannot afford a dispersion superior in dispersibility.

<Evaluation of Dispersibility of Dispersion>

[Evaluation 1: Compatibility with Water]

An N-acyl basic amino acid dispersion (20 mg) was placed in a beaker (50 mL), deionized water (20 mL) was added and the mixture was stirred with a magnetic stirrer for 30 seconds. The mixture was stood still and the time necessary for the entire crystals to either settle at the bottom or float at the surface, with no observable suspending crystals, was measured. Compatibility with water was evaluated according to the following evaluation criteria.

⊚: not less than 30 min
○: not less than 15 min and less than 30 min
Δ: not less than 1 min and less than 15 min
x: less than 1 min

[Evaluation 2: Visual Evaluation]

An N-acyl basic amino acid dispersion was placed in a 50 mL transparent glass vial (diameter 3.5 cm, height 5.5 cm) to a total amount of 50 g, the dispersion was visually observed and evaluated according to the following evaluation criteria.

⊚○: entirely white or pearly liquid or cream with no separation of liquid
⊚: entirely white or pearly liquid or cream with separation of liquid of thickness 5 mm or less in any of the surface, middle layer and bottom surface
○: entirely white or pearly liquid or cream with separation of liquid of thickness 5 mm-20 mm in any of the surface, middle layer and bottom surface
Δ: separation of liquid of thickness exceeding 20 mm is observed
x: crystals are floating on the surface or setting on bottom surface <Evaluation of Cosmetic Containing Dispersion>

The cosmetic cream of the following Table 1 was prepared, compared with control free of an N-acyl basic amino acid dispersion, and evaluated for smooth texture, absorbency (shortness of time until slimyness disappears) and absence of greasiness (greasiness of skin when application is completed) according to the following evaluation criteria.

⊚: remarkably superior to control
○: superior to control
Δ: equivalent to control
x: inferior to control

TABLE 1

|  | control | Example or Comparative Example |
|---|---|---|
| squalane | 5.00 | 5.00 |
| jojoba oil | 5.00 | 5.00 |
| macadamia nut oil | 5.00 | 5.00 |
| glyceryl tri(caprate/caprylate) | 5.00 | 5.00 |
| di(phytosteryl/octyldodecyl)lauroylglutamate | 1.00 | 1.00 |
| isostearyl hydroxystearate | 2.00 | 2.00 |
| shea butter | 2.00 | 2.00 |
| stearylalcohol | 3.80 | 3.80 |
| carnauba wax | 0.10 | 0.10 |
| glyceryl stearate | 2.90 | 2.90 |
| xanthan gum | 0.20 | 0.20 |
| water | 40.00 | 40.00 |
| sucrose palmitate | 0.40 | 0.40 |
| sodium stearoylglutamate (3% aq.) | 5.00 | 5.00 |
| cocoylarginineethylpyrrolidone-carboxylic acid (1% aq.) | 5.00 | 5.00 |
| N-acyl basic amino acid dispersion | 0.00 | 5.00 |
| citric acid | q.s. (adjusted to pH 5) | q.s. (adjusted to pH 5) |
| sodium hydroxide | q.s. (adjusted to pH 5) | q.s. (adjusted to pH 5) |
| water | balance | balance |
| total | 100.00 | 100.00 |

<Evaluation of Shampoo Containing the Dispersion>

The shampoo of the following Table 2 was prepared, and visually evaluated for white turbidity and liquid stability according to the following criteria. Sensory evaluation of foamability, rinsability (quickness of rinsing) and hair softness during rinsing were performed based on the comparison with the control free of the N-acyl basic amino acid dispersion, and according to the following criteria.

[white turbidity/pearlization (condition on the next day of preparation)]

○: strong white turbid/pearlized and uniform as a whole
Δ: somewhat transparent but white turbid/pearlized, or more or less nonuniform dispersion state
x: highly transparent and pearlized/unclear white turbid, or highly nonuniform dispersion state
xx: transparent, or layer partitioned due to floating/settling, or markedly nonuniform dispersion state

[liquid stability (condition after 1 month at 45° C.)]

⊙: uniformly dispersed, white turbid/pearlized

○: slightly nonuniform outermost layer or bottom layer

Δ: white turbid/pearlized as a whole, though floating/settling has started x: transparent due to dissolution, or phase separation by floating/settling, markedly nonuniform due to agglomeration

[foaming, quickness of rinsing, hair softness after rinsing]

⊙: remarkably superior to control

○: superior to control

Δ: equivalent to control x: inferior to control

TABLE 2

|  | control | Example or Comparative Example |
|---|---|---|
| laurylglucoside (50%) | 9.0 | 9.0 |
| disodium cocoylglutamate (25%) | 20.0 | 20.0 |
| sodium laurylsulfoacetate | 4.0 | 4.0 |
| magnesium chloride | 1.5 | 1.5 |
| glyceryl caprate | 3.0 | 3.0 |
| N-acyl basic amino acid dispersion | — | 5.0 |
| citric acid | q.s. (adjusted to pH 5) | q.s. (adjusted to pH 5) |
| sodium hydroxide | q.s. (adjusted to pH 5) | q.s. (adjusted to pH 5) |
| water | balance | balance |
| total | 100.0 | 100.0 |

Preparation of Dispersion

Dispersion of Example 2

Sodium hydroxide (2.4 g) was dissolved in water (25.6 g) at room temperature, and the mixture was heated to about 35° C. $N^\epsilon$-lauroyllysine (12.0 g) was added and dissolved at the same temperature (Component A). Thereafter, the solution was cooled to 25° C., and added dropwise to N-cocoylglutamic acid monotriethanolamine salt (30% aqueous solution, 60.0 g) (Component B) over 15 min to give the dispersion of Example 2.

Dispersions of Examples 3-7 and Comparative Examples 2-5

The dispersions of Examples 3-7 and Comparative Examples 2-5 were prepared by mixing Component A and Component B at the ratios (wt %) shown in Table 3 and in the same manner as in Example 2 by adding Component A to Component B.

Dispersion of Example 8

Sodium hydroxide (3.0 g) was dissolved in water (32.0 g) at room temperature, and the mixture was heated to about 35° C. $N^\epsilon$-Lauroyllysine (15.0 g) was added and dissolved at the same temperature (Component A). Then, the solution was cooled to 25° C., and a 40% aqueous citric acid solution (50.0 g) (Component B) was added dropwise thereto at about 5 g/min to give the dispersion of Example 8.

Dispersions of Examples 9-20 and Comparative Examples 6-15

The dispersions of Examples 9-20 and Comparative Examples 6-15 were prepared by preparing Component A at the ratios (wt %) shown in Table 4 and Table 5 and in the same manner as in Example 8, adding Component B dropwise thereto at about 5 g/min, and thereafter adding Component B' dropwise at about 5 g/min.

Dispersions of Examples 22-25

In the same manner as in Example 8 except that the rate of dropwise addition was changed to those shown in Table 6, the dispersions of Examples 22-25 were prepared.

Dispersion of Example 28

Sodium hydroxide (2.7 g) was dissolved in water (34.8 g) at room temperature, and the mixture was heated to about 35° C. $N^\epsilon$-Lauroyllysine (12.5 g) was added and dissolved at the same temperature. Thereafter, the solution was cooled to 25° C., and laurylglucoside (50% aqueous solution, 25.0 g) was added to give a uniform solution (Component A). N-Cocoylglutamic acid monosodium salt (30% aqueous solution, 5.0 g) and citric acid (30% aqueous solution, 20.2 g) were mixed at the same temperature (Component B), and Component B was added dropwise to Component A over 15 min to give the dispersion of Example 28.

Dispersions of Examples 26, 27 and 29-33, and Comparative Examples 16-20

In the same manner as in Example 28, Component A and Component B were respectively dissolved at the ratios (wt %) shown in Table 7, and Component B was added to Component A to give the dispersions of Examples 26, 27 and 29-33, and Comparative Examples 16-20.

Dispersions of Examples 34-40

The dispersions of Examples 34-40 were prepared by preparing Component A at the ratios (wt %) shown in Table 8 and in the same manner as in Example 28, adding Component B dropwise thereto at about 5 g/min, adjusting the pH to 6, and thereafter adding Component B' to the total amount of 100 g.

An N-acyl basic amino acid dispersion was placed in a 50 mL transparent glass vial (diameter 3.5 cm, height 5.5 cm) to a total amount of 50 g, and the viscosity of the dispersion placed in the 50 mL vial was measured using a B-type viscometer No. 4 spindle (manufactured by Tokimec Inc) at 25° C.

The diameter mode of $N^\epsilon$-lauroyllysine contained in the dispersion was measured using a laser diffraction/scattering type particle size distribution measurement apparatus LA-950 manufactured by Horiba, Ltd. For the measurement, a flow cell was used, and ion exchange water was used as a dispersion medium. The mode of diameter is a particle size at which the obtained frequency distribution curve shows the maximum level.

TABLE 3

| | | Ex. 2 | Ex. 3 | Ex. 4 | Ex. 5 | Ex. 6 | Ex. 7 | Comp. Ex. 2 | Comp. Ex. 3 | Comp. Ex. 4 | Comp. Ex. 5 |
|---|---|---|---|---|---|---|---|---|---|---|---|
| Component A | water | 25.6 | 21.3 | 32.0 | 30.0 | 32.0 | 30.0 | 32.0 | 28.0 | 28.0 | 28.0 |
| | sodium hydroxide | 2.4 | 2.0 | 3.0 | 2.8 | 3.0 | 2.8 | 3.0 | — | — | — |
| | $N^\epsilon$-lauroyllysine | 12.0 | 10.0 | 15.0 | 14.0 | 15.0 | 14.0 | 15.0 | 12.0 | — | — |
| | boron nitride | — | — | — | — | — | — | — | — | 12.0 | — |
| | molybdenum sulfate | — | — | — | — | — | — | — | — | — | 12.0 |
| Component B | water | — | 58.2 | 40.0 | 41.7 | 31.0 | — | 36.0 | — | — | — |
| | cocoylglutamic acid monotriethanolamine salt (30%) | 60.0 | — | — | — | — | — | — | 60.0 | 60.0 | 60.0 |
| | ascorbic acid | — | 8.5 | — | — | — | — | — | — | — | — |
| | citric acid | — | — | 10.0 | — | — | — | — | — | — | — |
| | 2-pyrrolidone-5-carboxylic acid | — | — | — | 11.5 | — | — | — | — | — | — |
| | lactic acid (90%) | — | — | — | — | 19.0 | — | — | — | — | — |
| | sodium glutamate (40%) | — | — | — | — | — | 54.0 | — | — | — | — |
| | hydrochloric acid (35%) | — | — | — | — | — | — | 14.0 | — | — | — |
| | acid/base (mol/mol) | 1.25 | 1.00 | 2.08 | 1.27 | 2.53 | 2.74 | 1.80 | — | — | — |
| | pH | 8.6 | 7.5 | 4.4 | 3.7 | 3.6 | 9.9 | <1 | 6.0 | 6.0 | 6.0 |
| | viscosity at 3 rpm/viscosity at 30 rpm | 5.2 | 6.5 | 5.9 | 5.9 | 5.7 | 5.6 | um | um | nm | nm |
| | mode diameter (μm) | 18.7 | nm | 54.8 | 31.9 | 21.4 | nm | 14.2 | 27.7 | nm | nm |
| dispersibility | compatibility with water | ⊙ | ⊙ | ⊙ | ○ | ⊙ | ⊙ | um (lump) | nm | nm | nm |
| | visual evaluation (next day) | ○ | ⊙ | ⊙○ | ○ | ○ | ⊙ | um (solidified) | X | X | X |
| | visual evaluation (1 week later) | ○ | ⊙ | ○ | ○ | ○ | nm | um (solidified) | X | X | X |
| evaluation of cosmetic containing dispersion | smooth texture | ⊙ | ⊙ | ⊙ | ⊙ | ⊙ | ⊙ | X | nm | nm | nm |
| | absorbency | ⊙ | ○ | ⊙ | ○ | ○ | ⊙ | X | nm | nm | nm |
| | not greasy | ○ | ○ | ⊙ | ○ | ○ | ⊙ | X | nm | nm | nm | nm: not measured
um: unmeasurable

The results of Table 3 have clarified that the dispersions of Examples 2-7, obtained by dissolving $N^\epsilon$-lauroyllysine in an aqueous sodium hydroxide solution and neutralizing the mixture with an organic acid, show dispersibility superior to that of the dispersion of Comparative Example 2 neutralized with hydrochloric acid. This is considered to be attributable to the low pH, which was not more than 1, of the dispersion neutralized with hydrochloric acid. In addition, a comparison of the dispersion of Example 2 obtained by dissolving $N^\epsilon$-lauroyllysine in aqueous sodium hydroxide solution, and neutralizing the solution with N-cocoylglutamic acid monotriethanolamine salt, and the dispersion of Comparative Example 3 obtained by simple mixing has clarified that a simple mixing cannot afford a dispersion superior in the dispersibility. Even the dispersions using a known lubricant powder such as boron nitride and molybdenum compound (Comparative Examples 4 and 5) failed to provide a stable dispersion. In addition, cosmetics containing the dispersions of Examples 2-7 showed good effects in the smooth texture, absorbency and greasiness. Particularly, Examples 2, 4 and 7 using a cocoylglutamic acid monotriethanolamine salt, citric acid and sodium glutamate, respectively, showed good results.

TABLE 4

| | | Ex. 8 | Ex. 9 | Ex. 10 | Ex. 11 | Ex. 12 | Ex. 13 | Ex. 14 | Ex. 15 | Ex. 16 |
|---|---|---|---|---|---|---|---|---|---|---|
| Component A | water | 32.00 | 32.00 | 32.00 | 32.00 | 32.00 | 32.00 | 32.00 | 36.00 | 20.00 |
| | sodium hydroxide | 3.00 | 3.00 | 3.00 | 3.00 | 3.00 | 3.00 | 3.00 | 4.00 | 2.00 |
| | $N^\epsilon$-lauroyllysine | 15.00 | 15.00 | 15.00 | 15.00 | 15.00 | 15.00 | 15.00 | 20.00 | 10.00 |
| Component B | citric acid (40%) | 50.00 | 40.00 | 30.00 | 22.50 | 20.00 | 17.50 | 15.00 | 40.00 | 20.00 |
| Component B' | trisodium citrate | — | — | — | — | — | — | — | — | — |
| | water | 0.00 | 10.00 | 20.00 | 27.50 | 30.00 | 32.50 | 35.00 | 0.0 | 48.0 |
| | acid/base (mol/mol) | 4.16 | 3.33 | 2.50 | 1.87 | 1.67 | 1.46 | 1.25 | 2.50 | 2.50 |
| | pH | 3.0 | 3.3 | 4.1 | 4.7 | 5.1 | 5.6 | 11.9 | 4.1 | 4.1 |
| | viscosity at 3 rpm/viscosity at 30 rpm | 6.5 | 6.8 | 6.2 | 5.9 | 6.6 | 6.4 | 5.8 | 6.9 | 5.1 |
| | mode diameter (μm) | 21.3 | 12.3 | 32.0 | 54.8 | 41.9 | 54.9 | 72.7 | nm | nm |
| dispersibility | compatibility with water | ⊙ | ⊙ | ⊙ | ⊙ | ⊙ | ⊙ | ○ | ○ | ○ |
| | visual evaluation (next day) | ○ | ⊙ | ⊙ | ⊙ | ⊙ | ⊙ | ⊙ | ⊙ | ○ |
| | visual evaluation (1 week later) | ○ | ⊙ | ⊙ | ○ | ⊙○ | ⊙○ | ○ | ⊙ | ⊙ |
| evaluation of cosmetic containing dispersion | smooth texture | ⊙ | ⊙ | ⊙ | ⊙ | ⊙ | ⊙ | ○ | ⊙ | ⊙ |
| | absorbency | ○ | ⊙ | ⊙ | ⊙ | ⊙ | ⊙ | Δ | ⊙ | ⊙ |
| | not greasy | ○ | ⊙ | ⊙ | ⊙ | ⊙ | ⊙ | Δ | ⊙ | ⊙ |

TABLE 4-continued

|  |  | Comp. Ex. 6 | Comp. Ex. 7 | Comp. Ex. 8 | Comp. Ex. 9 | Comp. Ex. 10 |
|---|---|---|---|---|---|---|
| Component A | water | 32.00 | 32.00 | — | — | — |
|  | sodium hydroxide | 3.00 | 3.00 | — | — | — |
|  | $N^\epsilon$-lauroyllysine | 15.00 | 15.00 | 15.00 | 15.00 | 15.00 |
| Component B | citric acid (40%) | 12.50 | 10.00 | 28.00 | 10.50 | 5.50 |
| Component B' | trisodium citrate | — | — | 6.46 | 6.46 | 6.46 |
|  | water | 37.50 | 40.00 | 50.54 | 68.04 | 73.04 |
|  | acid/base (mol/mol) | 1.04 | 0.83 | — | — | — |
|  | pH | 13.3 | 13.4 | 3.2 | 4.8 | 5.8 |
|  | viscosity at 3 rpm/viscosity at 30 rpm | 1.2 | 1.2 | um | um | um |
|  | mode diameter (μm) | nm | 83.0 | 27.7 | 27.7 | 27.7 |
| dispersibility | compatibility with water | Δ | X | X | X | X |
|  | visual evaluation (next day) | ○ | ○ | X | X | X |
|  | visual evaluation (1 week later) | ⊙ | Δ | nm | nm | nm |
| evaluation of cosmetic containing dispersion | smooth texture | X | X | Δ | Δ | Δ |
|  | absorbency | X | X | ○ | ○ | ○ |
|  | not greasy | Δ | Δ | Δ | Δ | Δ | nm: not measured
um: unmeasurable

TABLE 5

|  |  | Ex. 17 | Ex. 18 | Ex. 19 | Ex. 20 | Comp. Ex. 11 | Comp. Ex. 12 | Comp. Ex. 13 | Comp. Ex. 14 | Comp. Ex. 15 |
|---|---|---|---|---|---|---|---|---|---|---|
| Component A | water | 32.0 | 32.0 | 32.0 | 32.0 | 32.0 | 32.0 | — | — | — |
|  | sodium hydroxide | 3.0 | 3.0 | 3.0 | 3.0 | 3.0 | 3.0 | — | — | — |
|  | $N^\epsilon$-lauroyllysine | 15.0 | 15.0 | 15.0 | 15.0 | 15.0 | 15.0 | 15.0 | 15.0 | 15.0 |
| Component B | L-pyrrolidonecarboxylic acid (50%) | 48.0 | 25.0 | 20.0 | 19.4 | 18.0 | 16.0 | 5.6 | 0.6 | — |
| Component B' | sodium L-pyrrolidonecarboxylate (50%) | — | — | — | — | — | — | 22.8 | 22.8 | 22.8 |
|  | water | 2.0 | 25.0 | 30.0 | 30.6 | 32.0 | 34.0 | 56.60 | 61.60 | 62.20 |
|  | acid/base (mol/mol) | 2.48 | 1.29 | 1.03 | 1.00 | 0.93 | 0.83 | — | — | — |
|  | pH | 3.7 | 3.9 | 4.8 | 11.8 | 13.0 | 13.3 | 4.0 | 5.0 | 11.6 |
|  | viscosity at 3 rpm/viscosity at 30 rpm | 5.8 | 5.9 | 7.5 | 6.0 | 2.2 | 1.9 | um | um | um |
|  | mode diameter (μm) | 24.3 | 31.9 | 36.3 | 42.3 | 48.0 | 63.4 | 27.7 | 27.7 | 27.7 |
| dispersibility | compatibility with water | Δ | ⊙ | ⊙ | ○ | X | X | X | X | X |
|  | visual evaluation (next day) | ⊙ | ○ | ○ | ○ | ⊙○ | ⊙ | X | X | X |
|  | visual evaluation (1 week later) | ⊙ | ○ | ○ | ○ | ⊙○ | ⊙ | X | X | X |
| evaluation of cosmetic containing dispersion | smooth texture | Δ | ⊙ | ⊙ | ○ | X | X | Δ | Δ | Δ |
|  | absorbency | ○ | ⊙ | ⊙ | ○ | X | X | ○ | ○ | ○ |
|  | not greasy | ○ | ⊙ | ⊙ | ○ | Δ | Δ | Δ | Δ | Δ | um: unmeasurable

The results of Table 4 and Table 5 reveal that the dispersions of Examples 8-16 having a pH of 2 to 12 are superior in dispersibility. In addition, the results of Table 5 reveal that one or more equivalents of an acid needs to be added relative to the base. Comparative Examples 8-10 and 13-15, wherein the dispersions were obtained by simple mixing without neutralization, failed to provide a dispersion superior in dispersibility.

Figure 3:
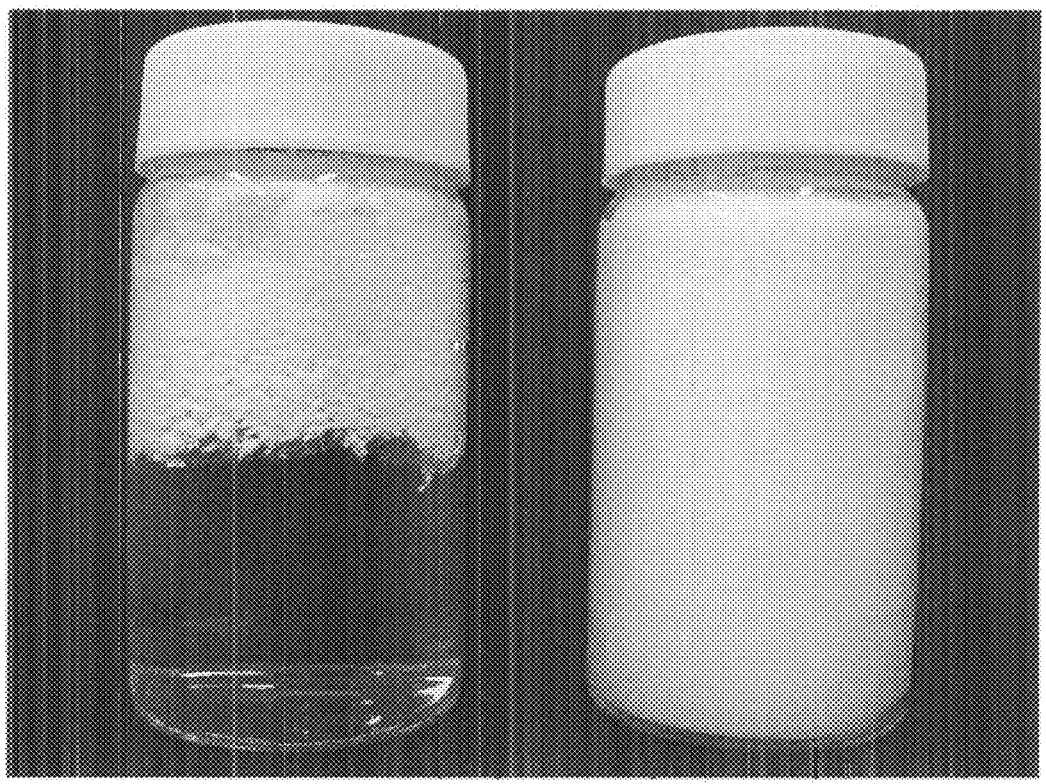
FIG. 3 shows photographs of erected images of the dispersions of Example 9 (right) and Comparative Example 8 (left) after a lapse of one week.
Figure 4:
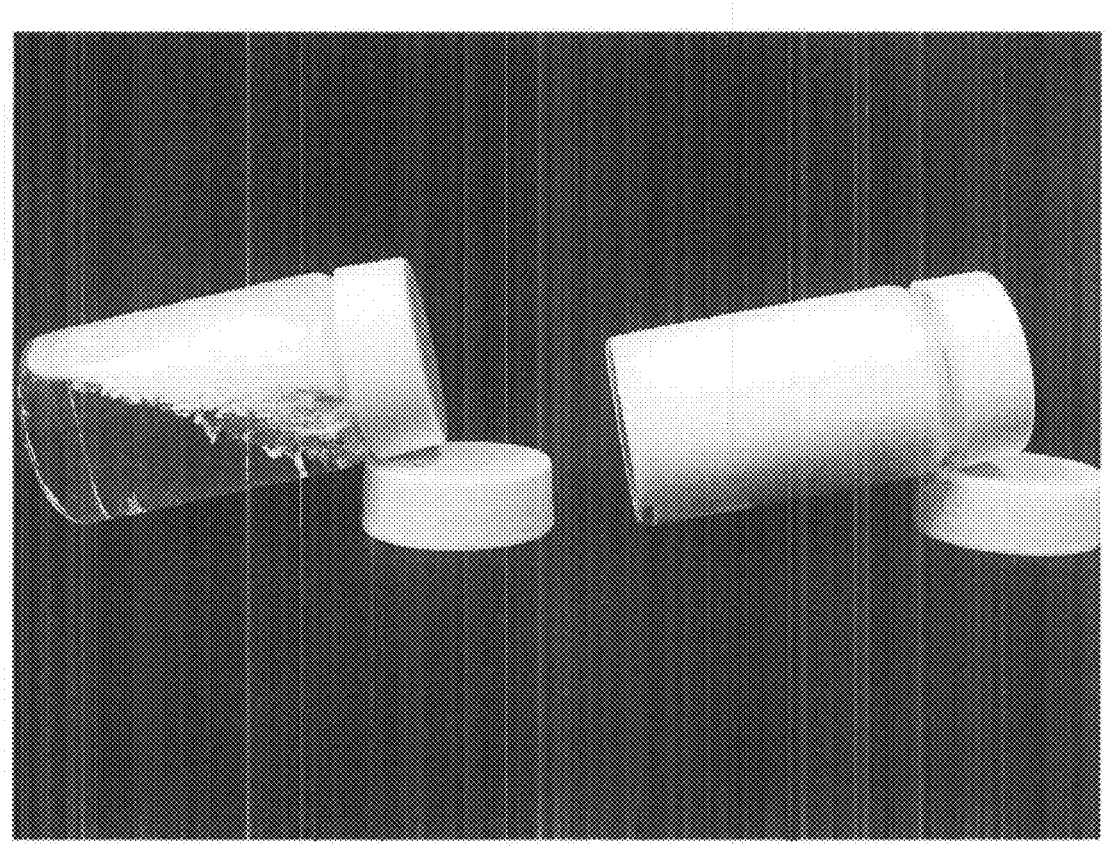
FIG. 4 shows photographs of the obliquely placed dispersions of Example 9 (right) and Comparative Example 8 (left) after a lapse of one week.

FIG. 3 shows photographs of erected images of the dispersions of Example 9 (right) and Comparative Example 8 (left) after a lapse of one week, and FIG. 4 shows photographs of the obliquely placed dispersions of Example 9 (right) and Comparative Example 8 (left) after a lapse of one week. The dispersions of Example 9 showed a creamy appearance, and were free of separation. However, the dispersions of Comparative Example 8 could not disperse $N^\epsilon$-lauroyllysine. It has been clarified therefore that a simple mixing cannot afford a dispersion superior in dispersibility.

TABLE 6

|  |  | Ex. 8 | Ex. 22 | Ex. 23 | Ex. 24 | Ex. 25 |
|---|---|---|---|---|---|---|
| Component A | water | 32.0 | 32.0 | 32.0 | 32.0 | 32.0 |
|  | sodium hydroxide | 3.0 | 3.0 | 3.0 | 3.0 | 3.0 |
|  | $N^\epsilon$-lauroyllysine | 15.0 | 15.0 | 15.0 | 15.0 | 15.0 |
| Component B | citric acid (40%) | 50.0 | 50.0 | 50.0 | 50.0 | 50.0 |
|  | acid/base (mol/mol) | 4.16 | 4.16 | 4.16 | 4.16 | 4.16 |
|  | pH | 3.0 | 3.0 | 3.0 | 3.0 | 3.0 |
|  | viscosity at 3 rpm/viscosity at 30 rpm | 6.5 | 6.4 | 6.0 | 6.1 | 5.7 |
|  | speed of acid addition mmol/s/1 dl | 0.52 | 0.23 | 0.15 | 0.12 | 0.10 |

TABLE 6-continued

|  |  | Ex. 8 | Ex. 22 | Ex. 23 | Ex. 24 | Ex. 25 |
|---|---|---|---|---|---|---|
| dispersibility | compatibility with water | ⊙ | ⊙ | ⊙ | ⊙ | ⊙ |
|  | visual evaluation (next day) | ⊙ | ⊙ | ⊙ | ⊙ | ⊙ |
|  | visual evaluation (1 week later) | ○ | ○ | ○ | ○ | ○ |

TABLE 6-continued

|  |  | Ex. 8 | Ex. 22 | Ex. 23 | Ex. 24 | Ex. 25 |
|---|---|---|---|---|---|---|
| evaluation of cosmetic containing dispersion | smooth texture | ⊙ | ⊙ | ⊙ | ⊙ | ⊙ |
|  | absorbency | ○ | ○ | ○ | ○ | ○ |
|  | not greasy | ○ | ○ | ○ | ○ | ○ |

The results of Table 6 reveal that the dispersion of the present invention can be obtained by dropwise addition of an acid at not less than 0.1 mmol/sec per 1 dl of the N-acyl basic amino acid solution.

TABLE 7

|  |  | Ex. 26 | Ex. 27 | Ex. 28 | Ex. 29 | Ex. 30 | Ex. 31 | Ex. 32 | Ex. 33 |
|---|---|---|---|---|---|---|---|---|---|
| Component A | water | 34.8 | 24.8 | 34.8 | 64.8 | 47.4 | 55.4 | 8.6 | 48.5 |
|  | $N^\epsilon$-lauroyllysine | 12.5 | 12.5 | 12.5 | 12.5 | 12.5 | 12.5 | 20.0 | 5.0 |
|  | sodium hydroxide | 2.7 | 2.7 | 2.7 | 2.7 | 2.7 | 2.7 | 4.0 | 1.1 |
|  | laurylglucoside (50%) | 15.0 | 40.0 | 25.0 | — | 10.0 | 2.0 | — | 30.0 |
|  | decylglucoside (50%) | 15.0 | — | — | — | — | — | 30.0 | — |
| Component B | sodium cocoylglutamate (30%) | — | — | 5.0 | — | — | — | — | — |
|  | citric acid (30%) | 20.0 | 20.0 | 20.0 | 20.0 | 20.0 | 20.0 | 30.0 | 8.0 |
|  | acid/base (mol/mol) | 1.39 | 1.39 | 1.31 | 1.39 | 1.39 | 1.39 | 1.39 | 1.39 |
|  | pH | 6.0 | 6.0 | 6.0 | 6.0 | 6.0 | 6.0 | 6.0 | 6.0 |
| dispersibility | compatibility with water | ⊙ | ⊙ | ⊙ | ⊙ | ⊙ | ⊙ | ⊙ | ⊙ |
|  | visual evaluation (next day) | ⊙○ | ⊙○ | ⊙○ | ⊙○ | ⊙○ | ⊙○ | ⊙○ | ⊙○ |
|  | visual evaluation (1 week later) | ⊙○ | ⊙○ | ⊙○ | ⊙○ | ⊙ | ⊙ | ⊙ | ○ |
|  | visual evaluation (3 months later) | ⊙○ | ⊙○ | ⊙○ | ○ | ○ | ○ | ○ | ○ |
|  | visual evaluation (45° C., 6 months later) | ⊙ | ⊙ | ⊙○ | Δ | ⊙ | ○ | ⊙ | ○ |
| evaluation of shampoo containing dispersion | white turbid/pearlized | ○ | ○ | ○ | Δ | ○ | ○ | ○ | X |
|  | liquid stability | ⊙ | ⊙ | ○ | Δ | ⊙ | ○ | ○ | ○ |
|  | foamability | ⊙ | ⊙ | ⊙ | ○ | ⊙ | ⊙ | ⊙ | ○ |
|  | rinsability | ⊙ | ⊙ | ⊙ | ○ | ⊙ | ⊙ | ○ | ○ |

|  |  | Comp. Ex. 16 | Comp. Ex. 17 | Comp. Ex. 18 | Comp. Ex. 19 | Comp. Ex. 20 |
|---|---|---|---|---|---|---|
| Component A | water | balance | balance | balance | balance | balance |
|  | $N^\epsilon$-lauroyllysine | 12.5 | 12.5 | 12.5 | — | — |
|  | sodium hydroxide | — | — | — | 2.7 | 2.7 |
|  | laurylglucoside (50%) | 15.0 | 40.0 | 25.0 | 15.0 | — |
|  | decylglucoside (50%) | 15.0 | — | — | 15.0 | 30.0 |
| Component B | sodium cocoylglutamate (30%) | — | — | 5.0 | — | — |
|  | citric acid (30%) | q.s. | q.s. | q.s. | 20.0 | 20.0 |
|  | acid/base (mol/mol) | — | — | — | — | — |
|  | pH | 6.0 | 6.0 | 6.0 | 6.0 | 6.0 |
| dispersibility | compatibility with water | Δ | Δ | Δ | nm | nm |
|  | visual evaluation (next day) | Δ | Δ | Δ | nm | nm |
|  | visual evaluation (1 week later) | nm | nm | nm | nm | nm |
|  | visual evaluation (3 months later) | nm | nm | nm | nm | nm |
|  | visual evaluation (45° C., 6 months later) | nm | nm | nm | nm | nm |
| evaluation of shampoo containing dispersion | white turbid/pearlized | Δ | Δ | X | X | X |
|  | liquid stability | X | X | X | nm | nm |
|  | foamability | Δ | Δ | Δ | X | Δ |
|  | rinsability | Δ | Δ | ○ | Δ | Δ | nm: not measured

TABLE 8

|  |  | Ex. 34 | Ex. 35 | Ex. 36 | Ex. 37 | Ex. 38 | Ex. 39 | Ex. 40 |
|---|---|---|---|---|---|---|---|---|
| Component A | water | 17.8 | 17.8 | 17.8 | 17.8 | 17.8 | 17.8 | 17.8 |
|  | $N^\epsilon$-lauroyllysine | 10.0 | 10.0 | 10.0 | 10.0 | 10.0 | 10.0 | 10.0 |
|  | sodium hydroxide | 2.2 | 2.2 | 2.2 | 2.2 | 2.2 | 2.2 | 2.2 |
|  | sodium laureth sulfate (27%) | 37.0 | — | — | — | — | — | — |
|  | disodium cocoylglutamate (25%) | — | 40.0 | — | — | — | — | — |
|  | cocamidopropylbetaine (30%) | — | — | 33.0 | — | — | — | — |
|  | sodium cocoamphoacetate (30%) | — | — | — | 33.0 | — | — | — |
|  | cocobetaine (30%) | — | — | — | — | 33.0 | — | — |
|  | cetyltrimethylammonium chloride (30%) | — | — | — | — | — | 33.0 | — |
|  | cocamide DEA | — | — | — | — | — | — | 10.0 |

TABLE 8-continued

| | | Ex. 34 | Ex. 35 | Ex. 36 | Ex. 37 | Ex. 38 | Ex. 39 | Ex. 40 |
|---|---|---|---|---|---|---|---|---|
| Component B | citric acid (30%) | q.s. | q.s. | q.s. | q.s. | q.s. | q.s. | q.s. |
| Component B' | water | balance | balance | balance | balance | balance | balance | balance |
| | total | 100.0 | 100.0 | 100.0 | 100.0 | 100.0 | 100.0 | 100.0 |
| | pH | 6 | 6 | 6 | 6 | 6 | 6 | 6 |
| dispersibility | compatibility with water | ⊙ | ⊙ | ⊙ | ⊙ | ⊙ | ⊙ | ⊙ |
| | next day | ⊙○ | ⊙○ | ⊙○ | ⊙○ | ⊙○ | ⊙○ | ⊙○ |
| | 1 week later | ⊙○ | ⊙○ | ⊙○ | ⊙○ | ⊙○ | ⊙○ | ⊙○ |
| | 3 months later | ⊙○ | ⊙○ | ⊙○ | ⊙○ | ⊙○ | ⊙○ | ⊙○ |
| | 45° C., 6 months later | ⊙○ | ⊙○ | ⊙ | ⊙○ | ⊙○ | ⊙○ | ⊙○ |
| evaluation of shampoo containing dispersion | white turbid/pearlized | ○ | Δ | ○ | ○ | ○ | ○ | ○ |
| | liquid stability | Δ | ○ | Δ | ⊙ | ⊙ | ○ | ⊙ |
| | foamability | ⊙ | ⊙ | ⊙ | ⊙ | ⊙ | ○ | ⊙ |
| | rinsability | ⊙ | ⊙ | ⊙ | ⊙ | ⊙ | ○ | ○ |

The results of Table 7 reveal that the dispersions of Examples 26-33, obtained by dissolving N-lauroyllysine in aqueous sodium hydroxide solution and adding a surfactant, were superior in dispersibility, and the dispersion of Example 28 using a cocoylglutamic acid monosodium salt as an organic acid was particularly fine.

The results of Table 8 reveal that the dispersions of Examples 34-40, obtained by dissolving N-lauroyllysine in sodium hydroxide, and adding various surfactants, were all superior in dispersibility, and the dispersions of Examples 36 and 38 containing a betaine-type amphoteric surfactant were particularly fine.

<Evaluation of Lubricity of the Dispersion>

Component A and Component B were respectively dissolved at the ratios (wt %) shown in Table 9, and Component B was added to Component A to give the dispersions of Example 41 and Comparative Examples 21 and 22. Lubricating ability when they were applied to a hard surface was evaluated according to the following criteria.

A dispersion (10 mL) was uniformly applied onto 8 cm×11 cm aluminum foil, and a weight with a PET container (basal area 70.25 cm$^2$) containing water to adjust the total weight of the container and water to 500 g was placed thereon. The force (g) necessary for starting move of the weight by pulling the foil was measured with a spring balance, and the lubricity was evaluated according to the following criteria.
⊙: less than 20 g
○: not less than 20 g and less than 80 g
Δ: not less than 80 g and less than 150 g
x: not less than 150 g

TABLE 9

| | | Example 41 | Comparative Example 21 | Comparative Example 22 |
|---|---|---|---|---|
| Component A | water | 36.4 | 32 | 37 |
| | sodium hydroxide | 0.6 | 3 | — |
| | N$^ε$-lauroyllysine | 3 | 15 | 3 |
| Component B | cocoylglutamic acid monotriethanolamine salt (30%) | 60 | — | 60 |
| | water | — | 36 | — |
| | hydrochloric acid (35%) | — | 14 | — |
| | lubricity (measurement value) | ⊙(<1) | X(150) | Δ(87) |
| | pH of dispersion | 7 | <1 | 6 |

The results of Table 9 reveal that the dispersion of Example 41, obtained by dissolving N$^ε$-lauroyllysine in aqueous sodium hydroxide solution and neutralizing, the mixture with an organic acid, has an extremely high lubricity, as compared to the dispersion of Comparative Example 22 obtained by simple mixing. In addition, Example 41 obtained by neutralization with an organic acid showed a high lubricity as compared to the dispersion of Comparative Example 21 obtained by neutralization with an inorganic acid (hydrochloric acid).

<Evaluation 1 of Cosmetic Containing the Dispersion>

The dispersion of Example 2 in Table 3 was actually added to a shampoo, and the lubricity when the hair was treated with the shampoo was evaluated according to the following criteria.

A hairpiece (European virgin brown hair, 5 g) was washed with sodium dodecyl sulfate, dried and combed over, and the force (g) necessary for the combing was measured (blank). Then, the hairpieces were washed with the shampoos of Example and Comparative Example. Thereafter, the hairpiece was dried and combed, and the force (g) necessary for the combing was measured, based on which a rate of change was determined. The rate of change was calculated by (after shampoo-blank)/(blank)×100.
⊙: less than −20%
○: not less than −20% and less than −10%
Δ: not less than −10% and less than 0%
x: not less than 0%

TABLE 10

| | Example 42 | Example 43 | Comparative Example 22 | Comparative Example 23 |
|---|---|---|---|---|
| commercially available shampoo for adult | 99 | — | 100 | — |
| commercially available shampoo for baby | — | 99 | — | 100 |
| dispersion of Example 2 | 1 | 1 | — | — |
| dry combability (rate of change) | ⊙ (−40) | ⊙ (−60) | X (60) | X (20) |

The results of Table 10 reveal that the shampoo added with the dispersion of Example 2 required a less force for combing as compared to the shampoo without the dispersion of Example 2, and the force was remarkably lower than the blank. Thus, it has been clarified that the dispersion of the present invention improves dry combability when added to a shampoo. The components of the shampoo added with the dispersion of Example 2 are as follows, each of which was stable at room temperature for 3 month.

Commercially available shampoo for adult: Suave (manufactured by Helene Curtis): Ammonium Lauryl Sulfate, Ammomium Lauryl Ether Sulfate, Sodium Cocamide Mipa Sulfosuccinate Commercially available shampoo for baby: Baby Shampoo (manufactured by Johnson&Johnson): Peg-80 Sorbitan Laurate, Cocamido Propyl Betaine, Sodium Trideceth Sulfate, Lauro Amphoacetate <Evaluation 2 of Cosmetic Containing the Dispersion>

The dispersion of Example 26 was actually added to a shampoo, and evaluated according to the aforementioned criteria.

TABLE 11

|  |  | Ex. 44 | Ex. 45 | Ex. 46 | Ex. 47 | Ex. 48 | Comp. Ex. 24 | Comp. Ex. 25 | Comp. Ex. 26 |
|---|---|---|---|---|---|---|---|---|---|
|  | N-cocoylalanine TEA (30%) | 46.0 | 46.0 | 46.0 | 46.0 | 46.0 | 46.0 | 46.0 | 46.0 |
|  | cocamidopropylbetaine (30%) | 2.0 | 2.0 | 2.0 | 2.0 | 2.0 | 2.0 | 2.0 | 2.0 |
|  | sodium cocoamphoacetate (30%) | 2.0 | 2.0 | 2.0 | 2.0 | 2.0 | 2.0 | 2.0 | 2.0 |
|  | laurylglucoside (50%) | — | — | — | — | — | 0.75 | 0.75 | 0.015 |
|  | decylglucoside (50%) | — | — | — | — | — | 0.75 | 0.75 | 0.015 |
|  | $N^\varepsilon$-lauroyllysine | — | — | — | — | — | 0.0 | 1.25 | 0.025 |
|  | glycerol | 2.0 | 2.0 | 2.0 | 2.0 | 2.0 | 2.0 | 2.0 | 2.0 |
|  | PCA sodium (50%) | 1.0 | 1.0 | 1.0 | 1.0 | 1.0 | 1.0 | 1.0 | 1.0 |
|  | glyceryl caprate | 5.0 | 5.0 | 5.0 | 5.0 | 5.0 | 5.0 | 5.0 | 5.0 |
|  | distearic acid PEG-150 | 1.0 | 1.0 | 1.0 | 1.0 | 1.0 | 1.0 | 1.0 | 1.0 |
|  | methylparaben | 0.2 | 0.2 | 0.2 | 0.2 | 0.2 | 0.2 | 0.2 | 0.2 |
|  | sodium benzoate | 0.2 | 0.2 | 0.2 | 0.2 | 0.2 | 0.2 | 0.2 | 0.2 |
|  | water | balance | balance | balance | balance | balance | balance | balance | balance |
|  | dispersion of Ex. 26 | 10.0 | 5.0 | 2.0 | 1.0 | 0.2 | 0.0 | 0.0 | 0.0 |
|  | total | 100.0 | 100.0 | 100.0 | 100.0 | 100.0 | 100.0 | 100.0 | 100.0 |
|  | $N^\varepsilon$-lauroyllysine amount | 1.250 | 0.625 | 0.250 | 0.125 | 0.025 | 0.000 | 1.250 | 0.025 |
| evaluation of shampoo containing dispersion | white turbid/pearlized | ○ | ○ | Δ | Δ | X | XX (transparent) | X | XX |
|  | liquid stability | ○ | ○ | ○ | Δ | X (transparent) | X (transparent) | X (settling) | X (transparent) |
|  | foamability | ⊙ | ⊙ | ○ | Δ | Δ | Δ | Δ | Δ |
|  | rinsability | ⊙ | ⊙ | ⊙ | ⊙ | ○ | Δ | ○ | Δ |
|  | hair softness during rinsing | ○ | ○ | ⊙ | ⊙ | ⊙ | Δ | Δ | Δ |

Formulation Example 1

A shampoo was produced by the formulation shown in Table 12. The shampoo shows good wet and dry combability.

TABLE 12

| laurylglucoside (50%) | 9 |
|---|---|
| disodium lauroylglutamate (25%) | 20 |
| sodium laurylsulfoacetate | 4 |
| glyceryl caprate | 3 |
| dispersion of Example 28 | 5 |
| $N^\alpha$-lauroylarginine | 0.2 |
| magnesium chloride | 1.5 |
| citric acid | to pH 5.5 |
| water | balance |
| total | 100 |

Formulation Example 2

A body shampoo was produced by the formulation shown in Table 13.

Components A and B were dissolved in advance by heating, and D was prepared as a dispersion in advance. B was added to A, then C was added, and finally, D was added to complete the shampoo. When in use, the shampoo afforded excellent foamability, and refreshed touch of skin after drying. The body shampoo was stable during preservation at 45° C.

TABLE 13

| A | disodium N-cocoylglutamate (25%) | 20 |
|---|---|---|
|  | sodium lauroamphoacetate (39%) | 3 |
|  | glyceryl caprate | 2.5 |
|  | L-PCA sodium (50%) | 1 |
|  | water | balance |
|  | preservative | q.s. |

TABLE 13-continued

| B | $N^\varepsilon$-lauroyllysine | 0.5 |
|---|---|---|
|  | sodium hydroxide | 0.1 |
|  | water | 1.6 |
| C | citric acid (20%) | 4.3 |
| D | 1,3-propanediol | 10 |
|  | guar gum | 0.5 |
|  | xanthan gum | 0.3 |
|  | total | 100 |

Formulation Example 3

A cutting oil was produced by the formulation shown in Table 14.

TABLE 14

| dispersion of Example 2 | 98.0 |
|---|---|
| POE(10) isostearyl ether | 2.0 |
| total | 100.0 |

INDUSTRIAL APPLICABILITY

According to the present invention, an N-acyl basic amino acid dispersion superior in dispersibility can be obtained, and a dispersion containing an N-acyl basic amino acid at a high concentration can be obtained. Utilizing the dispersion, moreover, an N-acyl basic amino acid can be blended with a cosmetic such as shampoo and the like or a cutting oil without causing problems of agglomeration and settling, whereby a cosmetic or cutting oil superior in dispersibility and improved in smooth texture can be obtained.

In addition, using an organic acid as the acid, an N-acyl basic amino acid dispersion can be obtained easily, and a dispersion more superior in lubricity can be obtained. By utilizing the dispersion, a cosmetic or cutting oil superior in smooth texture can be obtained.

The invention claimed is:

1. A method of producing an N-acyl basic amino acid dispersion having a pH of 2 to 12, which comprises:
   (1) dissolving at least one N-acyl basic amino acid in a basic solution, wherein said basic solution comprises a base, to obtain an N-acyl basic amino acid solution; and
   (2) mixing said N-acyl basic amino acid solution with one or more equivalents of at least one organic acid based on the equivalent of said base in said basic solution,
   wherein said N-acyl basic amino acid solution comprises a surfactant, and
   said at least one organic acid is selected from the group consisting of lactic acid, citric acid, ascorbic acid, 2-pyrrolidone-5-carboxylic acid, cocoylglutamic acid monotriethanolamine salt, and sodium glutamate.

2. The method according to claim 1, wherein said N-acyl basic amino acid is present in said dispersion in a concentration of 3 to 30 wt %.

3. The method according to claim 1, wherein said dispersion has a (viscosity at 3 rpm)/(viscosity at 30 rpm) ratio within the range of 4 to 30.

4. The method according to claim 1, wherein said base is sodium hydroxide or potassium hydroxide, and said base is present in said N-acyl basic amino acid solution in an amount of 0.05 g to 1 g per 1 g of said N-acyl basic amino acid.

5. The method according to claim 1, wherein said surfactant is an alkylglucoside.

6. The method according to claim 1, wherein said N-acyl basic amino acid is $N^\epsilon$-lauroyllysine.

7. The method according to claim 1, wherein said organic acid is added dropwise to said N-acyl basic amino acid solution at a rate of not less than 0.1 mmol/sec per 1 dl of said N-acyl basic amino acid solution.

8. A method of producing an N-acyl basic amino acid dispersion, which comprises:
   (1) dissolving an N-acyl basic amino acid in an alkaline solution having a pH of 9 or more, to obtain an N-acyl basic amino acid solution; and
   (2) adjusting the pH of said N-acyl basic amino acid solution to 4 to 8 with at least one organic acid,
   wherein said N-acyl basic amino acid solution comprises a surfactant, and
   said at least one organic acid is selected from the group consisting of lactic acid, citric acid, ascorbic acid, 2-pyrrolidone-5-carboxylic acid, cocoylglutamic acid monotriethanolamine salt, and sodium glutamate.

* * * * *